US012612609B2

(12) United States Patent
Chen et al.

(10) Patent No.: US 12,612,609 B2
(45) Date of Patent: Apr. 28, 2026

(54) FnCpf1 MUTANT FOR BROAD-SPECTRUM IDENTIFICATION ON PAM SEQUENCE ANS USE THEREOF

(71) Applicant: INSTITUTE OF MICROBIOLOGY, CHINESE ACADEMY OF SCIENCES, Beijing (CN)

(72) Inventors: Zehua Chen, Beijing (CN); Ming Li, Beijing (CN)

(73) Assignee: INSTITUTE OF MICROBIOLOGY, CHINESE ACADEMY OF SCIENCES, Beijing (CN)

(*) Notice: Subject to any disclaimer, the term of this patent is extended or adjusted under 35 U.S.C. 154(b) by 84 days.

(21) Appl. No.: 17/911,646

(22) PCT Filed: Sep. 25, 2020

(86) PCT No.: PCT/CN2020/117860
§ 371 (c)(1),
(2) Date: Sep. 14, 2022

(87) PCT Pub. No.: WO2022/061748
PCT Pub. Date: Mar. 31, 2022

(65) Prior Publication Data
US 2023/0146044 A1      May 11, 2023

(51) Int. Cl.
  *C12N 9/22*          (2006.01)
  *C12N 15/70*         (2006.01)

(52) U.S. Cl.
  CPC .............. *C12N 9/22* (2013.01); *C12N 15/70* (2013.01); *C12N 2310/20* (2017.05); *C12N 2800/80* (2013.01)

(58) Field of Classification Search
  CPC ...................................................... C12N 9/22
  See application file for complete search history.

(56) References Cited

U.S. PATENT DOCUMENTS

2020/0109382 A1      4/2020   Zhang et al.
2021/0348144 A1*   11/2021   Zhang ...................... C12N 9/22

FOREIGN PATENT DOCUMENTS

CN        107312761 A     11/2017
CN        108486146 A      9/2018
CN        109593763 A      4/2019
CN        109790527 A      5/2019
CN        110799525 A      2/2020
CN        112111471 A     12/2020
WO       32018195545 A2    10/2018
WO       WO-2018195545 A2 *  10/2018   ............... C12N 9/22

OTHER PUBLICATIONS

Makarova et al., Evolutionary classification of CRISPR-Cas systems: a burst of class 2 and derived variants. Nature Reviews Microbiology (2020), 18: 67-83 (Year: 2020).*
Wang et al., Improved CRISPR-Cas 12a-assisted one-pot DNA editing method enables seamless DNA editing. Biotechnology and Bioengineering (2019), 116: 1463-1474 (Year: 2019).*
Kleinstiver et al., Engineered CRISPR-Cas12a variants with increased activities and improved targeting ranges for gene, epigenetic and base editing. Nature Biotechnology (2019), 37: 276-282 (Year: 2019).*
Gao et al., Engineered Cpf1 variants with altered PAM specificities. Nature Biotechnology (2017), 35: 789-792 (Year: 2017).*
Shindele et al., Engineering CRISPR/LbCas12a for highly efficient, temperature-tolerant plant gene editing. Plant Biotechnology Journal (2019), 18: 1118-1120 (Year: 2019).*
Zetsche et al., Cpf1 is a single RNA-guided endonuclease of a class 2 CRISPR-Cas system. Cell (2015), 163: 759-771 (Year: 2015).*
Toth et al., Improved LbCas12a variants with altered PAM specificities further broaden the genome targeting range of Cas12a nucleases. Nucleic Acids Research (2020), 48: 3722-3733 (Year: 2020).*
Nishimasu et al., Structural Basis for the Altered PAM Recognition by Engineered CRISPR-Cpf1. Molecular Cell (2017), 67: 138-147 (Year: 2017).*
Stella et al., Structure of the Cpf1 endonuclease R-loop complex after target DNA cleavage. Nature (2017), 546: 559-563 (Year: 2017).*
Swarts et al., Structural Basis for Guide RNA Processing and Seed-Dependent DNA Targeting by CRISPR-Cas12a. Molecular Cell (2017), 66: 221-233 (Year: 2017).*
Chen-Chen Zhou et al., "The new member of CRISPR Family, CRISPR-Cpf1" Prog. Biochem. Biophys. 2018; 45 (6),585-592 (Jun. 30, 2018).
Liping Wang et al. "Improved CRISPR!Cas12a!assisted one!pot DNA editing method enables seamless DNA editing" Biotechnology and Bioengineering, vol. 16, No. 116, pp. 1463-1474 (Feb. 11, 2019).

* cited by examiner

*Primary Examiner* — Catherine Konopka
(74) *Attorney, Agent, or Firm* — SZDC Law PC

(57)          ABSTRACT

Provided is a mutant of CRISPR nuclease FnCpf1. Compared with wild-type FnCpf1, the CRISPR nuclease FnCpf1 has the following mutations: K671R/E566V/D751G/N508H/N637S, K671R/E566V/D751G/F570L/N634D/R755K, K671R/E566V/D751G/S518G/K639R, K671R/E566V/D751G/F570L/E686D, K671R/E566V/D751G/K613N/N637S/N534K/G664V, K671R/E566V/D751G/K613N/F570L/G664S/N637Y, K671R/E566V/D751G/K613N/Y724C/F570L, or K671R/E566V/D751G/K613N/Y724C/F570L/R690I/L662I. The coding gene of the mutant has higher editing efficiency and wider editing range than the wild-type FnCpf1.

6 Claims, 3 Drawing Sheets
Specification includes a Sequence Listing.

SEQUENCE LISTING

```
<160> NUMBER OF SEQ ID NOS: 6

<210> SEQ ID NO 1
<211> LENGTH: 3903
<212> TYPE: DNA
<213> ORGANISM: Francisella novicida

<400> SEQUENCE: 1
atgtcaattt atcaagaatt tgttaataaa tatagtttaa gtaaaactct aagatttgag      60
ttaatcccac agggtaaaac acttgaaaac ataaaagcaa gaggtttgat tttagatgat     120
gagaaaagag ctaaagacta caaaaaggct aaacaaataa ttgataaata tcatcagttt     180
tttatagagg agatattaag ttcggtttgt attagcgaag atttattaca aaactattct     240
gatgtttatt ttaaacttaa aaagagtgat gatgataatc tacaaaaaga tttttaaaagt     300 gcaaaagata cgataaagaa acaaatatct gaatatataa aggactcaga gaaatttaag     360
aatttgttta atcaaaacct tatcgatgct aaaaaagggc aagagtcaga tttaattcta     420
tggctaaagc aatctaagga taatggtata gaactattta aagccaatag tgatatcaca     480
gatatagatg aggcgttaga aataatcaaa tcttttaaag gttggacaac ttattttaag     540
ggttttcatg aaaatagaaa aaatgtttat agtagcaatg atattcctac atctattatt     600
tataggatag tagatgataa tttgcctaaa tttctagaaa ataaagctaa gtatgagagt     660
ttaaaagaca aagctccaga agctataaac tatgaacaaa ttaaaaaaga tttggcagaa     720
gagctaacct ttgatattga ctacaaaaca tctgaagtta atcaaagagt tttttcactt     780
gatgaagttt ttgagatagc aaactttaat aattatctaa atcaaagtgg tattactaaa     840
```

-continued

```
tttaatacta ttattggtgg taaatttgta aatggtgaaa atacaaagag aaaaggtata    900
aatgaatata taaatctata ctcacagcaa ataaatgata aaacactcaa aaaatataaa    960
atgagtgttt tattttaagca aattttaagt gatacagaat ctaaatcttt tgtaattgat   1020
aagttagaag atgatagtga tgtagttaca acgatgcaaa gttttttatga gcaaatagca   1080 gcttttaaaa cagtagaaga aaaatctatt aaagaaacac tatctttatt atttgatgat   1140
ttaaaagctc aaaaacttga tttgagtaaa atttatttta aaaatgataa atctcttact   1200
gatctatcac aacaagtttt tgatgattat agtgttattg gtacagcggt actagaatat   1260
ataactcaac aaatagcacc taaaaatctt gataaccta gtaagaaaga gcaagaatta   1320
atagccaaaa aaactgaaaa agcaaaatac ttatctctag aaactataaa gcttgcctta   1380
gaagaattta ataagcatag agatatagat aaacagtgta ggtttgaaga atacttgca   1440 aactttgcgg ctattccgat gatatttgat gaaatagctc aaaacaaaga caatttggca   1500
cagatatcta tcaaatatca aaatcaaggt aaaaaagacc tacttcaagc tagtgcggaa   1560
gatgatgtta aagctatcaa ggatctttta gatcaaacta ataatctctt acataaaacta  1620 aaaatatttc atattagtca gtcagaagat aaggcaaata ttttagacaa ggatgagcat   1680
ttttatctag tatttgagga gtgctacttt gagctagcga atatagtgcc tctttataac   1740
aaaattagaa actatataac tcaaaagcca tatagtgatg agaaatttaa gctcaatttt    1800
gagaactcga ctttggctaa tggttgggat aaaaataaag agcctgacaa tacggcaatt    1860
ttatttatca aagatgataa atattatctg ggtgtgatga ataagaaaaa taacaaaata    1920
tttgatgata aagctatcaa agaaaataaa ggcgagggtt ataaaaaaat tgtttataaa    1980
cttttacctg gcgcaaataa aatgttacct aaggttttct tttctgctaa atctataaaa   2040
ttttataatc ctagtgaaga tatacttaga ataagaaatc attccacaca tacaaaaaat    2100
ggtagtcctc aaaaaggata tgaaaaattt gagtttaata ttgaagattg ccgaaaattt    2160
atagattttt ataaacagtc tataagtaag catccggagt ggaaagattt tggatttaga    2220
ttttctgata ctcaaagata taattctata gatgaatttt atagagaagt tgaaaatcaa    2280
ggctacaaac taacttttga aaatatatca gagagctata ttgatagcgt agttaatcag    2340
ggtaaattgt acctattcca aatctataat aaagattttt cagcttatag caaagggcga    2400
ccaaatctac atactttata ttggaaagcg ctgtttgatg agagaaatct tcaagatgtg    2460
gtttataagc taaatggtga ggcagagctt ttttatcgta aacaatcaat acctaaaaaa   2520
atcactcacc cagctaaaga ggcaaatagct aataaaaaca aagataatcc taaaaaagag   2580 agtgttttttg aatatgattt aatcaaagat aaacgcttta ctgaagataa gttttttcttt  2640 cactgtccta ttacaatcaa ttttaaatct agtggagcta ataagtttaa tgatgaaatc    2700
aatttattgc taaaagaaaa agcaaatgat gttcatatat taagtataga cagaggtgaa    2760
agacatttag cttactatac tttggtagat ggtaaaggca atatcatcaa acaagatact    2820
ttcaacatca ttggtaatga tagaatgaaa acaaactacc atgataagct tgctgcaata    2880
gagaaagata gggattcagc taggaaagac tggaaaaaga taaataacat caaagagatg    2940
aaagagggct atctatctca ggtagttcat gaaatagcta agctagttat agagtataat    3000
gctattgtgg tttttgagga tttaaatttt ggatttaaaa gagggcgttt caaggtagag    3060
aagcaggtct atcaaaagtt agaaaaaatg ctaattgaga aactaaacta tctagttttc   3120
aaagataatg agtttgataa aactggggga gtgcttagag cttatcagct aacagcacct   3180
tttgagactt ttaaaaagat gggtaaacaa acaggtatta tctactatgt accagctggt   3240
```

-continued

```
tttacttcaa aaatttgtcc tgtaactggt tttgtaaatc agttatatcc taagtatgaa    3300
agtgtcagca aatctcaaga gttctttagt aagtttgaca agatttgtta taaccttgat    3360
aagggctatt ttgagtttag ttttgattat aaaaactttg gtgacaaggc tgccaaaggc    3420
aagtggacta tagctagctt tgggagtaga ttgattaact ttagaaattc agataaaaat    3480
cataattggg atactcgaga agtttatcca actaaagagt tggagaaatt gctaaaagat    3540
tattctatcg aatatgggca tggcgaatgt atcaaagcag ctatttgcgg tgagagcgac    3600
aaaaagtttt ttgctaagct aactagtgtc ctaaatacta tcttacaaat gcgtaactca    3660
aaaacaggta ctgagttaga ttatctaatt tcaccagtag cagatgtaaa tggcaatttc    3720
tttgattcgc gacaggcgcc aaaaaatatg cctcaagatg ctgatgccaa tggtgcttat    3780
catattgggc taaaaggtct gatgctacta ggtaggatca aaaataatca agagggcaaa    3840
aaactcaatt tggttatcaa aaatgaagag tattttgagt tcgtgcagaa taggaataac    3900
tag                                                                  3903
```

```
<210> SEQ ID NO 2
<211> LENGTH: 1300
<212> TYPE: PRT
<213> ORGANISM: Francisella novicida

<400> SEQUENCE: 2

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
```

```
                    245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
                275                 280                 285

Phe Val Asn Gly Glu Asn Thr Lys Arg Lys Gly Ile Asn Glu Tyr Ile
                290                 295                 300

Asn Leu Tyr Ser Gln Gln Ile Asn Asp Lys Thr Leu Lys Lys Tyr Lys
            305                 310                 315                 320

Met Ser Val Leu Phe Lys Gln Ile Leu Ser Asp Thr Glu Ser Lys Ser
                    325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
                355                 360                 365

Ser Ile Lys Glu Thr Leu Ser Leu Leu Phe Asp Asp Leu Lys Ala Gln
            370                 375                 380

Lys Leu Asp Leu Ser Lys Ile Tyr Phe Lys Asn Asp Lys Ser Leu Thr
        385                 390                 395                 400

Asp Leu Ser Gln Gln Val Phe Asp Asp Tyr Ser Val Ile Gly Thr Ala
                    405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
                435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
        465                 470                 475                 480

Asn Phe Ala Ala Ile Pro Met Ile Phe Asp Glu Ile Ala Gln Asn Lys
                    485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Asp Val Lys Ala Ile Lys Asp
                515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
        545                 550                 555                 560

Phe Tyr Leu Val Phe Glu Glu Cys Tyr Phe Glu Leu Ala Asn Ile Val
                    565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
                595                 600                 605

Trp Asp Lys Asn Lys Glu Pro Asp Asn Thr Ala Ile Leu Phe Ile Lys
            610                 615                 620

Asp Asp Lys Tyr Tyr Leu Gly Val Met Asn Lys Lys Asn Asn Lys Ile
        625                 630                 635                 640

Phe Asp Asp Lys Ala Ile Lys Glu Asn Lys Gly Glu Gly Tyr Lys Lys
                    645                 650                 655

Ile Val Tyr Lys Leu Leu Pro Gly Ala Asn Lys Met Leu Pro Lys Val
                660                 665                 670
```

```
Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
        820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
        930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
        1010                1015                1020

Tyr Gln  Lys Leu Glu Lys Met  Leu Ile Glu Lys Leu  Asn Tyr Leu
        1025                1030                1035

Val Phe  Lys Asp Asn Glu Phe  Asp Lys Thr Gly Gly  Val Leu Arg
        1040                1045                1050

Ala Tyr  Gln Leu Thr Ala Pro  Phe Glu Thr Phe Lys  Lys Met Gly
        1055                1060                1065

Lys Gln  Thr Gly Ile Ile Tyr  Tyr Val Pro Ala Gly  Phe Thr Ser
        1070                1075                1080
```

-continued

```
Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300
```

```
<210> SEQ ID NO 3
<211> LENGTH: 750
<212> TYPE: DNA
<213> ORGANISM: Francisella novicida

<400> SEQUENCE: 3
ggtaaaaaag acctacttca agctagtgcg gaagatgatg ttaaagctat caaggatctt      60
ttagatcaaa ctaataatct cttacataaa ctaaaaatat ttcatattag tcagtcagaa     120
gataaggcaa atattttaga caaggatgag cattttatc tagtatttga ggagtgctac      180
tttgagctag cgaatatagt gcctctttat aacaaaatta gaaactatat aactcaaaag     240
ccatatagtg atgagaaatt taagctcaat tttgagaact cgactttggc taatggttgg     300
gataaaaata aagagcctga caatacggca attttattta tcaaagatga taaatattat     360
ctgggtgtga tgaataagaa aaataacaaa atatttgatg ataaagctat caaagaaaat     420
aaaggcgagg gttataaaaa aattgtttat aaacttttac ctggcgcaaa taaaatgtta     480
cctaaggttt tcttttctgc taaatctata aaattttata tcctagtga agatatactt      540 agaataagaa atcattccac acatacaaaa aatggtagtc ctcaaaaagg atatgaaaaa     600
tttgagttta atattgaaga ttgccgaaaa tttatagatt tttataaaca gtctataagt     660
aagcatccgg agtggaaaga ttttggattt agattttctg atactcaaag atataattct     720
atagatgaat tttatagaga agttgaaaat                                       750
```

-continued

<210> SEQ ID NO 4
<211> LENGTH: 3903
<212> TYPE: DNA
<213> ORGANISM: Francisella novicida

<400> SEQUENCE: 4

```
atgtcaattt atcaagaatt tgttaataaa tatagtttaa gtaaaactct aagatttgag        60
ttaatcccac agggtaaaac acttgaaaac ataaaagcaa gaggtttgat tttagatgat       120
gagaaaagag ctaaagacta caaaaaggct aaacaaataa ttgataaata tcatcagttt       180
tttatagagg agatattaag ttcggtttgt attagcgaag atttattaca aaactattct       240
gatgtttatt ttaaacttaa aaagagtgat gatgataatc tacaaaaaga tttttaaaagt       300 gcaaaagata cgataaagaa acaaatatct gaatatataa aggactcaga gaaatttaag       360
aatttgttta atcaaaacct tatcgatgct aaaaaagggc aagagtcaga tttaattcta       420
tggctaaagc aatctaagga taatggtata gaactattta aagccaatag tgatatcaca       480
gatatagatg aggcgttaga aataatcaaa tcttttaaag gttggacaac ttattttaag       540
ggttttcatg aaaatagaaa aaatgtttat agtagcaatg atattcctac atctattatt       600
tataggatag tagatgataa tttgcctaaa tttctagaaa taaagctaa gtatgagagt        660 ttaaaagaca aagctccaga agctataaac tatgaacaaa ttaaaaaaga tttggcagaa       720
gagctaacct ttgatattga ctacaaaaca tctgaagtta tcaaagagt tttttcactt        780 gatgaagttt ttgagatagc aaactttaat aattatctaa atcaaagtgg tattactaaa       840
tttaatacta ttattggtgg taaatttgta aatggtgaaa atacaaagag aaaaggtata       900
aatgaatata taaatctata ctcacagcaa ataaatgata aaacactcaa aaaatataaa       960
atgagtgttt tatttaagca aattttaagt gatacagaat ctaaatcttt tgtaattgat      1020
aagttagaag atgatagtga tgtagttaca acgatgcaaa gttttttatga gcaaatagca      1080 gctttttaaaa cagtagaaga aaaatctatt aaagaaacac tatctttatt atttgatgat      1140
ttaaaagctc aaaaacttga tttgagtaaa atttatttta aaaatgataa atctcttact      1200
gatctatcac aacaagtttt tgatgattat agtgttattg gtacagcggt actagaatat      1260
ataactcaac aaatagcacc taaaaatctt gataacccta gtaagaaaga gcaagaatta      1320
atagccaaaa aaactgaaaa agcaaaatac ttatctctag aaactataaa gcttgcctta      1380
gaagaattta ataagcatag agatatagat aaacagtgta ggtttgaaga atacttgca       1440 aactttgcgg ctattccgat gatatttgat gaaatagctc aaaacaaaga caatttggca      1500
cagatatcta tcaaatatca aaatcaaggt aaaaaagacc tacttcaagc tagtgcggaa      1560
gatgatgtta aagctatcaa ggatctttta gatcaaacta ataatctctt acataaaacta      1620 aaaatatttc atattagtca gtcagaagat aaggcaaata ttttagacaa ggatgagcat      1680
ttttatctag tatttgtgga gtgctacctt gagctagcga atatagtgcc tctttataac      1740
aaaattagaa actatataac tcaaaagcca tatagtgatg agaaatttaa gctcaatttt      1800
gagaactcga ctttggctaa tggttgggat aaaaataatg agcctgacaa tacggcaatt      1860
ttatttatca aagatgataa atattatctg ggtgtgatga ataagaaaaa taacaaaata      1920
tttgatgata aagctatcaa agaaaataaa ggcgagggtt ataaaaaaat tgtttataaa      1980
cttatacctg cgcaaataa aatgttacct cgtgtttttct tttctgctaa atctataaaa      2040
ttttataatc ctagtgaaga tatacttata ataagaaatc attccacaca tacaaaaaat      2100
ggtagtcctc aaaaaggata tgaaaaattt gagtttaata ttgaagattg ccgaaaattt      2160
```

-continued

```
atagattttt gtaaacagtc tataagtaag catccggagt ggaaagattt tggatttaga     2220
ttttctgata ctcaaagata taattctata ggtgaatttt atagagaagt tgaaaatcaa     2280
ggctacaaac taacttttga aaatatatca gagagctata ttgatagcgt agttaatcag     2340
ggtaaattgt acctattcca aatctataat aaagattttt cagcttatag caaagggcga     2400
ccaaatctac atactttata ttggaaagcg ctgtttgatg agagaaatct tcaagatgtg     2460
gtttataagc taaatggtga ggcagagctt ttttatcgta aacaatcaat acctaaaaaa     2520
atcactcacc cagctaaaga ggcaatagct aataaaaaca aagataatcc taaaaaagag     2580
agtgtttttg aatatgattt aatcaaagat aaacgcttta ctgaagataa gttttttcttt     2640 cactgtccta ttacaatcaa ttttaaatct agtggagcta ataagtttaa tgatgaaatc     2700
aatttattgc taaagaaaa agcaaatgat gttcatatat taagtatagc aagaggtgaa     2760
agacatttag cttactatac tttggtagat ggtaaaggca atatcatcaa acaagatact     2820
ttcaacatca ttggtaatga tagaatgaaa acaaactacc atgataagct tgctgcaata     2880
gagaaagata gggattcagc taggaaagac tggaaaaaga taaataacat caaagagatg     2940
aaagagggct atctatctca ggtagttcat gaaatagcta agctagttat agagtataat     3000
gctattgtgg ttttttgagga tttaaatttt ggatttaaaa gagggcgttt caaggtagag     3060
aagcaggtct atcaaaagtt agaaaaaatg ctaattgaga aactaaacta tctagttttc     3120
aaagataatg agtttgataa aactggggga gtgcttagag cttatcagct aacagcacct     3180
tttgagactt ttaaaaagat gggtaaacaa acaggtatta tctactatgt accagctggt     3240
tttacttcaa aaatttgtcc tgtaactggt tttgtaaatc agttatatcc taagtatgaa     3300
agtgtcagca aatctcaaga gttctttagt aagtttgaca agatttgtta taaccttgat     3360
aagggctatt ttgagtttag ttttgattat aaaaactttg gtgacaaggc tgccaaaggc     3420
aagtggacta tagctagctt tgggagtaga ttgattaact ttagaaattc agataaaaat     3480
cataattggg atactcgaga agtttatcca actaaagagt tggagaaatt gctaaaagat     3540
tattctatcg aatatgggca tggcgaatgt atcaaagcag ctatttgcgg tgagagcgac     3600
aaaaagtttt ttgctaagct aactagtgtc ctaaatacta tcttacaaat gcgtaactca     3660
aaaacaggta ctgagttaga ttatctaatt tcaccagtag cagatgtaaa tggcaatttc     3720
tttgattcgc gacaggcgcc aaaaaatatg cctcaagatg ctgatgccaa tggtgcttat     3780
catattgggc taaaaggtct gatgctacta ggtaggatca aaaataatca agagggcaaa     3840
aaactcaatt tggttatcaa aaatgaagag tattttgagt tcgtgcagaa taggaataac     3900
tag                                                                    3903
```

<210> SEQ ID NO 5
<211> LENGTH: 29
<212> TYPE: DNA
<213> ORGANISM: Artificial Sequence
<220> FEATURE:
<223> OTHER INFORMATION: dFnCpf1 mutation

<400> SEQUENCE: 5

```
accatcaccg attggagtgt tttgctggt                                          29
```

<210> SEQ ID NO 6
<211> LENGTH: 21
<212> TYPE: DNA
<213> ORGANISM: Artificial Sequence
<220> FEATURE:

-continued

<223> OTHER INFORMATION: Target site

<400> SEQUENCE: 6
gggcactctc cagatagggga t                                           21

FnCpf1 MUTANT FOR BROAD-SPECTRUM IDENTIFICATION ON PAM SEQUENCE ANS USE THEREOF

This application is the National Stage Application of PCT/CN2020/117860, filed on Sep. 25, 2020.

TECHNICAL FIELD

The invention relates to the field of biotechnology. In particular, the invention relates to mutants of CRISPR nuclease FnCpf1 and its application.

BACKGROUND OF THE INVENTION

CRISPR-Cas system has been a powerful genome editing tool to insert, delete, or modify the sequences of genome in a living organism since its conception. In order to improve the accuracy and editing efficiency of the fixed-point mutation, a single-base editing system combining CRISPR-Cas proteins with cytosine/adenine deaminase is recently developed as a new generation of more accurate gene-editing tools. The single-base editing technology can accurately and irreversibly transform from one base pair to another (C-to-T or A-to-G) without causing DNA double-strand breaks and homologous recombination. However, the limited availability of editable sites in the target bacterial genome and off-target activity have restrained the CRISPR/Cas BE system's applicability.

As an alternative CRISPR nuclease beyond the commonly used Cas9, Cpf1 offers potentially advantageous in multiplex gene targeting in the same cell due to its RNA endonuclease activity. The ability to simultaneously manipulate multiple genes is highly demanded to the system level, which enables the interrogation of much more complex interactions in genome-scale networks. Besides, the Cpf1 system displays some enticing features such as a more concise crRNA (~40 nt), smaller molecular weight, as well as low rates of off-target activity. Therefore, we believe that DNA enzyme inactivation of Cpf1 (dCpf1) has great potential as an effective tool for multi-gene regulation.

Nevertheless, Cpf1 mediated gene editing essentially requires the recognition of a T-rich PAM of form 5'-TTTV/TTV (V represents A, C, or G), which hinders its application in gene editing of GC-rich organisms. To address this limitation, two *Acidaminococcus* sp. Cpf1 (AsCpf1) variants RVR and RR were initially engineered to recognize alternative PAMs, i.e., TATV and TYCV, respectively. (Gao L, Cox D B T, Yan W X, Manteiga J C, Schneider M W, Yamano T, et al. Engineered Cpf1 variants with altered PAM specificities. Nat Biotechnol 2017; 35:789-92.) Later, the target range of AsCpf1 was further expanded to TTYN/VTTV/TRTV PAMs. (Kleinstiver B P, Sousa A A, Walton R T, Tak Y E, Hsu J Y, Clement K, et al. Engineered CRISPR-Cas12a variants with increased activities and improved targeting ranges for gene, epigenetic and base editing. Nat Biotechnol 2019; 37:276-82.) Besides, another widely used Cpf1 from Francisellanovicida (FnCpf1), was engineered to identify non-canonical PAMs, however the −4 T preference in the PAM sequence was ignored in the study. (Wang L, Wang H, Liu H, Zhao Q, Liu B, Wang L, et al. Improved CRISPR-Cas12a-assisted one-pot DNA editing method enables seamless DNA editing. Biotechnol Bioeng 2019; 116:1463-74.) Nevertheless, many PAMs remain inaccessible to Cpf1, especially the GC-rich PAM sequences. Thus, additional variants with expanded targeting capabilities are needed to enable applications requiring high targeting density and flexibility.

SUMMARY OF THE INVENTION

In view of the shortcomings of the existing technology, we designed a negative screening assay in *E. coli* to extend the PAM sequence preference for dFnCpf1 to the GC-rich PAMs. The resulting subset of dFnCpf1 mutants exhibited a higher recognition and binding for sites with non-canonical PAMs and retained robust activities on canonical TTTV PAMs.

The present invention provides a mutant of CRISPR nuclease FnCpf1, which exists the following mutations relative to wild-type FnCpf1 with amino acid sequence as shown in SEQ ID NO: 2: K671R/E566V/D751G/N508H/N637S, K671R/E566V/D751G/F570L/N634D/R755K, K671R/E566V/D751G/S518G/K639R, K671R/E566V/D751G/F570L/E686D, K671R/E566V/D751G/K613N/N637S/N534K/G664V, K671R/E566V/D751G/K613N/F570L/G664S/N637Y, K671R/E566V/D751G/K613N/Y724C/F570L, K671R/E566V/D751G/K613N/Y724C/F570L/R690I/L662I.

Preferably, the mutant has the following mutations relative to wild-type FnCpf1: K671R/E566V/D751G/K613N/Y724C/F570L/R690I/L662I. K671R/E566V/D751G/K613N/N637S/N534K/G664V, K671R/E566V/D751G/K613N/F570L/G664S/N637Y, K671R/E566V/D751G/K613N/Y724C/F570L Optimally, the mutation has the following mutations relative to wild-type FnCpf1: K671R/E566V/D751G/K613N/Y724C/F570L/R690I/L662I The invention further provides the coding gene of the mutants mentioned above. The nucleotide sequence is shown in SEQ ID NO:4.

The invention also provides vectors containing the above genes for gene editing.

Further, we provide a recombinant cell line containing the vectors, such as *Escherichia coli*, is provided.

The invention also provides applications of the aforementioned genes in gene editing such as base editing of bacterial genomes.

The mutants in our invention exhibit higher recognition and binding ability at sites of non-canonical PAMs compared with wild-type FnCpf1, while still maintaining robust activity at typical TTTV PAMs. Furthermore, we demonstrated that the mutants in our invention could be designed as cytosine base editor in multi-target genome editing in *E. coli* with higher efficiency and broader targeting range than wild-type FnCpf1. It indicates that the mutant in our invention has obvious advantages in the recognition range of PAM.

DETAILED DESCRIPTION OF THE PREFERRED EMBODIMENTS

Figures 1, 2:
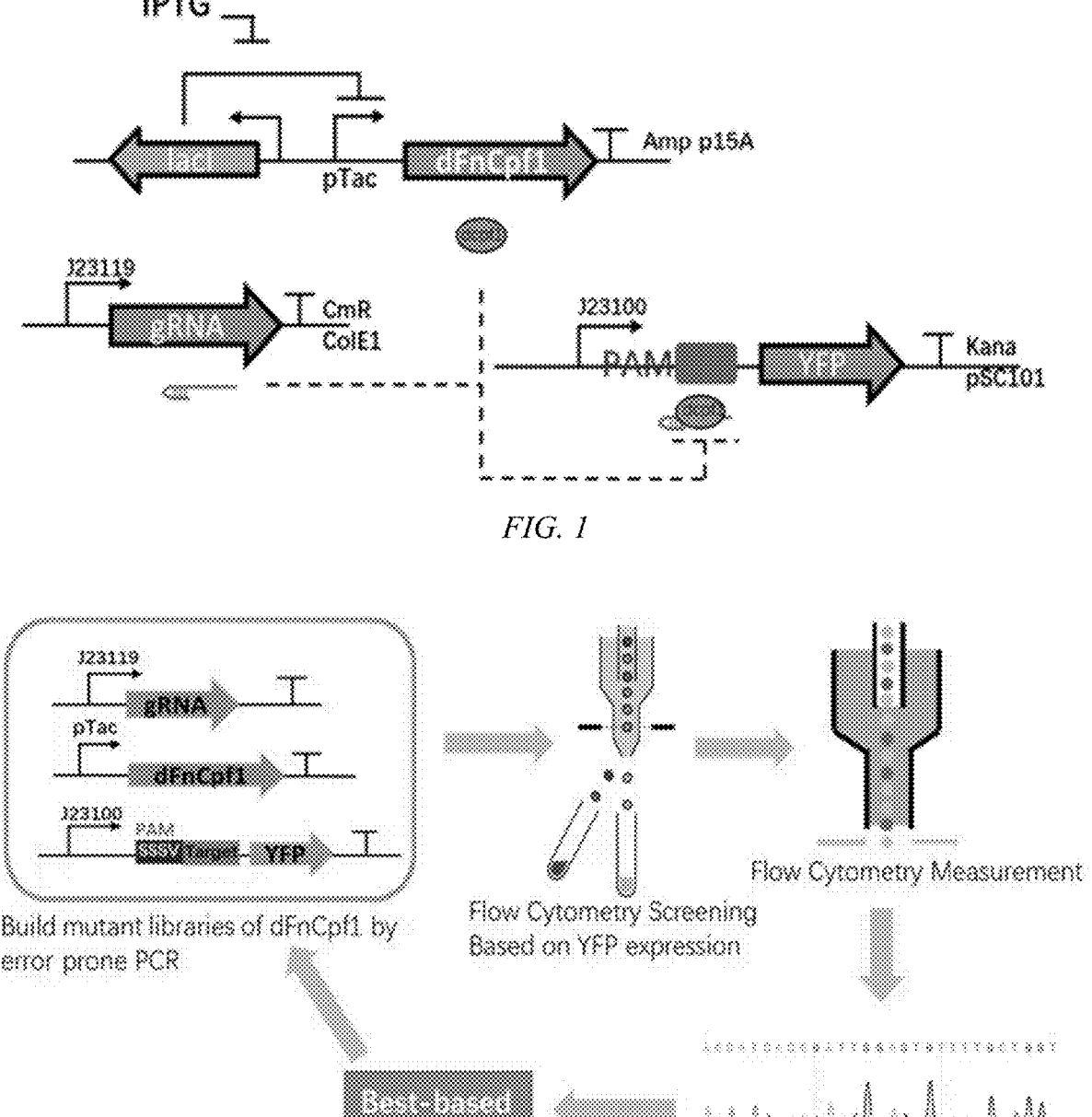
FIG. 1. Schematic representation of a dCpf1-interference YFP-based repression circuit in *E. coli*. In the circuit, dCpf1 was induced by IPTG and crRNA were expressed from a constitutive promoter (J23119), and a reporter gene YFP is repressed by the dFnCpf1-crRNA complex in the upstream region of its initial transcription. Therefore, the ability of dCpf1 mutants to recognize and bind PAM sequences can be quantified by the inhibition of YFP fluorescence values.
FIG. 2. Flow chart of the directed evolution of CRISPR nuclease dFnCpf1. The directed evolution process was to use error-prone PCR to construct dFnCpf1 mutation library, use flow cytometry to screen the bacteria with significantly reduced YFP fluorescence value and to further verify its inhibition efficiency. Then sequencing, and obtain the best mutant for the next round of directed evolution. The mutation sequence is ACCATCACCGATTG-GAGTGTTTTGCTGGT (SEQ ID NO:5).

In the following, the invention is further elaborated through the implementation scheme of research process to better understand the invention, but does not constitute a limitation on the invention.

We selected dFnCpf1 from Francisellanovicida for directed evolution, and focused on the −2 to −4 bits of the PAM sequence (the −1 bit base was not considered because of the large selectivity), then tried to extend the PAM sequence preference to the GC-rich PAMs.

Sequences of dFnCpf1 is provided as follows (SEQ ID NO:1):

```
ATGTCAATTTATCAAGAATTTGTTAATAAATATAGTTTAAGTAAAACTCTAAGATTTG

AGTTAATCCCACAGGGTAAAACACTTGAAAACATAAAAGCAAGAGGTTTGATTTT

AGATGATGAGAAAAGAGCTAAAGACTACAAAAAGGCTAAACAAATAATTGATAAA

TATCATCAGTTTTTTATAGAGGAGATATTAAGTTCGGTTTGTATTAGCGAAGATTTAT

TACAAAACTATTCTGATGTTTATTTTAAACTTAAAAAGAGTGATGATGATAATCTAC

AAAAAGATTTTAAAAGTGCAAAAGATACGATAAAGAAACAAATATCTGAATATATA

AAGGACTCAGAGAAATTTAAGAATTTGTTTAATCAAAACCTTATCGATGCTAAAAA

AGGGCAAGAGTCAGATTTAATTCTATGGCTAAAGCAATCTAAGGATAATGGTATAG

AACTATTTAAAGCCAATAGTGATATCACAGATATAGATGAGGCGTTAGAAATAATCA

AATCTTTTAAAGGTTGGACAACTTATTTTAAGGGTTTTCATGAAAATAGAAAAAAT

GTTTATAGTAGCAATGATATTCCTACATCTATTATTTATAGGATAGTAGATGATAATTT

GCCTAAATTTCTAGAAAATAAAGCTAAGTATGAGAGTTTAAAAGACAAAGCTCCA

GAAGCTATAAACTATGAACAAATTAAAAAAGATTTGGCAGAAGAGCTAACCTTTG

ATATTGACTACAAAACATCTGAAGTTAATCAAAGAGTTTTTTCACTTGATGAAGTT

TTTGAGATAGCAAACTTTAATAATTATCTAAATCAAAGTGGTATTACTAAATTTAATA

CTATTATTGGTGGTAAATTTGTAAATGGTGAAAATACAAAGAGAAAAGGTATAAAT

GAATATATAAATCTATACTCACAGCAAATAAATGATAAAACACTCAAAAAATATAAA

ATGAGTGTTTTATTTAAGCAAATTTTAAGTGATACAGAATCTAAATCTTTTGTAATT

GATAAGTTAGAAGATGATAGTGATGTAGTTACAACGATGCAAAGTTTTTATGAGCA

AATAGCAGCTTTTAAAACAGTAGAAGAAAATCTATTAAAGAAACACTATCTTTAT

TATTTGATGATTTAAAAGCTCAAAAACTTGATTTGAGTAAAATTTATTTTAAAAATG

ATAAATCTCTTACTGATCTATCACAACAAGTTTTTGATGATTATAGTGTTATTGGTAC

AGCGGTACTAGAATATATAACTCAACAAATAGCACCTAAAAATCTTGATAACCCTA

GTAAGAAAGAGCAAGAATTAATAGCCAAAAAAACTGAAAAAGCAAATACTTATC

TCTAGAAACTATAAAGCTTGCCTTAGAAGAATTTAATAAGCATAGAGATATAGATAA
```

-continued

```
ACAGTGTAGGTTTGAAGAAATACTTGCAAACTTTGCGGCTATTCCGATGATATTTG

ATGAAATAGCTCAAAACAAAGACAATTTGGCACAGATATCTATCAAATATCAAAAT

CAAGGTAAAAAAGACCTACTTCAAGCTAGTGCGGAAGATGATGTTAAAGCTATCA

AGGATCTTTTAGATCAAACTAATAATCTCTTACATAAACTAAAAATATTTCATATTAG

TCAGTCAGAAGATAAGGCAAATATTTTAGACAAGGATGAGCATTTTTATCTAGTATT

TGAGGAGTGCTACTTTGAGCTAGCGAATATAGTGCCTCTTTATAACAAAATTAGAA

ACTATATAACTCAAAAGCCATATAGTGATGAGAAATTTAAGCTCAATTTTGAGAACT

CGACTTTGGCTAATGGTTGGGATAAAAATAAAGAGCCTGACAATACGGCAATTTTA

TTTATCAAAGATGATAAATATTATCTGGGTGTGATGAATAAGAAAAATAACAAAATA

TTTGATGATAAAGCTATCAAAGAAAATAAAGGCGAGGGTTATAAAAAAATTGTTTA

TAAACTTTTACCTGGCGCAAATAAAATGTTACCTAAGGTTTTCTTTTCTGCTAAATC

TATAAAATTTTATAATCCTAGTGAAGATATACTTAGAATAAGAAATCATTCCACACAT

ACAAAAAATGGTAGTCCTCAAAAAGGATATGAAAAATTTGAGTTTAATATTGAAGA

TTGCCGAAAATTTATAGATTTTTATAAACAGTCTATAAGTAAGCATCCGGAGTGGAA

AGATTTTGGATTTAGATTTTCTGATACTCAAAGATATAATTCTATAGATGAATTTTAT

AGAGAAGTTGAAAATCAAGGCTACAAACTAACTTTTGAAAATATATCAGAGAGCT

ATATTGATAGCGTAGTTAATCAGGGTAAATTGTACCTATTCCAAATCTATAATAAAGA

TTTTTCAGCTTATAGCAAAGGGCGACCAAATCTACATACTTTATATTGGAAAGCGCT

GTTTGATGAGAGAAATCTTCAAGATGTGGTTTATAAGCTAAATGGTGAGGCAGAGC

TTTTTTATCGTAAACAATCAATACCTAAAAAAATCACTCACCCAGCTAAAGAGGCA

ATAGCTAATAAAAACAAAGATAATCCTAAAAAAGAGAGTGTTTTTGAATATGATTT

AATCAAAGATAAACGCTTTACTGAAGATAAGTTTTTCTTTCACTGTCCTATTACAAT

CAATTTTAAATCTAGTGGAGCTAATAAGTTTAATGATGAAATCAATTTATTGCTAAA

AGAAAAAGCAAATGATGTTCATATATTAAGTATAGACAGAGGTGAAAGACATTTAG

CTTACTATACTTTGGTAGATGGTAAAGGCAATATCATCAAACAAGATACTTTCAACA

TCATTGGTAATGATAGAATGAAAACAAACTACCATGATAAGCTTGCTGCAATAGAG

AAAGATAGGGATTCAGCTAGGAAAGACTGGAAAAAGATAAATAACATCAAAGAG

ATGAAAGAGGGCTATCTATCTCAGGTAGTTCATGAAATAGCTAAGCTAGTTATAGA

GTATAATGCTATTGTGGTTTTTGAGGATTTAAATTTTGGATTTAAAAGAGGGCGTTT

CAAGGTAGAGAAGCAGGTCTATCAAAAGTTAGAAAAAATGCTAATTGAGAAACTA

AACTATCTAGTTTTCAAAGATAATGAGTTTGATAAAACTGGGGGAGTGCTTAGAGC

TTATCAGCTAACAGCACCTTTTGAGACTTTTAAAAAGATGGGTAAACAAACAGGT

ATTATCTACTATGTACCAGCGGTTTTACTTCAAAAATTTGTCCTGTAACTGGTTTTG

TAAATCAGTTATATCCTAAGTATGAAAGTGTCAGCAAATCTCAAGAGTTCTTTAGTA

AGTTTGACAAGATTTGTTATAACCTTGATAAGGGCTATTTTGAGTTTAGTTTTGATT

ATAAAAACTTTGGTGACAAGGCTGCCAAAGGCAAGTGGACTATAGCTAGCTTTGG

GAGTAGATTGATTAACTTTAGAAATTCAGATAAAAATCATAATTGGGATACTCGAG

AAGTTTATCCAACTAAAGAGTTGGAGAAATTGCTAAAAGATTATTCTATCGAATATG

GGCATGGCGAATGTATCAAAGCAGCTATTTGCGGTGAGAGCGACAAAAAGTTTTT

TGCTAAGCTAACTAGTGTCCTAAATACTATCTTACAAATGCGTAACTCAAAAACAG

GTACTGAGTTAGATTATCTAATTTCACCAGTAGCAGATGTAAATGGCAATTTCTTTG
```

-continued

ATTCGCGACAGGCGCCAAAAAATATGCCTCAAGATGCTGATGCCAATGGTGCTTAT

CATATTGGGCTAAAAGGTCTGATGCTACTAGGTAGGATCAAAAATAATCAAGAGGG

CAAAAAACTCAATTTGGTTATCAAAAATGAAGAGTATTTTGAGTTCGTGCAGAATA

GGAATAACTAG.

A 750 bp DNA sequence which is randomly mutagenized through error-prone PCR is provided as follow (SEQ ID NO: 3):

GGTAAAAAAGACCTACTTCAAGCTAGTGCGGAAGATGATGTTAAAGCTAT

CAAGGATCTTTTAGATCAAACTAATAATCTCTTACATAAACTAAAAATAT

TTCATATTAGTCAGTCAGAAGATAAGGCAAATATTTTAGACAAGGATGAG

CATTTTTATCTAGTATTTGAGGAGTGCTACTTTGAGCTAGCGAATATAGT

GCCTCTTTATAACAAAATTAGAAACTATATAACTCAAAAGCCATATAGTG

ATGAGAAATTTAAGCTCAATTTTGAGAACTCGACTTTGGCTAATGGTTGG

GATAAAAATAAAGAGCCTGACAATACGGCAATTTTATTTATCAAAGATGA

-continued

TAAATATTATCTGGGTGTGATGAATAAGAAAAATAACAAAATATTTGATG

ATAAAGCTATCAAAGAAAATAAAGGCGAGGGTTATAAAAAAATTGTTTAT

AAACTTTTACCTGGCGCAAATAAAATGTTACCTAAGGTTTTCTTTTCTGC

TAAATCTATAAAATTTTATAATCCTAGTGAAGATATACTTAGAATAAGAA

ATCATTCCACACATACAAAAAATGGTAGTCCTCAAAAAGGATATGAAAAA

TTTGAGTTTAATATTGAAGATTGCCGAAAATTTATAGATTTTTATAAACA

GTCTATAAGTAAGCATCCGGAGTGGAAAGATTTTGGATTTAGATTTTCTG

ATACTCAAAGATATAATTCTATAGATGAATTTTTATAGAGAAGTTGAAAAT.

The above DNA sequence encodes 1300 amino acid residues, and the amino acid sequence (SEQ ID NO: 2) is as follows:

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVEN

QGYKLTFENISESYIDSVVNQGKLYLFQIYNKDFSAYSKGRPNLHTLYWKALFDERNL

QDVVYKLNGEAELFYRKQSIPKKITHPAKEAIANKNKDNPKKESVFEYDLIKDKRFTE

DKFFFHCPITINFKSSGANKFNDEINLLLKEKANDVHILSIDRGERHLAYYTLVDGKGN

IIKQDTFNIIGNDRMKTNYHDKLAAIEKDRDSARKDWKKINNIKEMKEGYLSQVVHE

IAKLVIEYNAIVVFEDLNFGFKRGRFKVEKQVYQKLEKMLIEKLNYLVFKDNEFDKT

GGVLRAYQLTAPPFETFKKMGKQTGIIYYVPAGFTSKICPVTGFVNQLYPKYESVSKSQ

EFFSKFDKICYNLDKGYFEFSFDYKNFGDKAAKGKWTIASFGSRLINFRNSDKNHNW

DTREVYPTKELEKLLKDYSIEYGHGECIKAAICGESDKKFFAKLTSVLNTILQMRNSK

TGTELDYLISPVADVNGNFFDSRQAPKNMPQDADANGAYHIGLKGLMLLGRIKNNQ

EGKKLNLVIKNEEYFEFVQNRNN.

Embodiment 1

First of all, we developed a bacterial negative screening assay where a constitutively expressed yfp gene was targeted in the upstream region of its initial transcription by a crRNA. Gibson Assembly or Golden Gate Assembly was employed to construct plasmids used in this study. The plasmid sequences were confirmed via Sanger sequencing. A 750 bp DNA sequence (SEQ ID NO: 3) from dFnCpf1 was randomly mutagenized through error-prone PCR to construct a dfncpf1 variants library. Later, the PCR products were inserted into the modified the Repressor Generator Plasmid (RGP) containing a pTac inducible promoter, a p15A replication origin, and an ampicillin-selectable marker using the Golden Gate method. The vector was used to control the inducible expression of dCpf1 enzymes. The crRNA plasmid contained a synthetic constitutive promoter J23119, a ColE1 replication origin, and a chloramphenicol-selectable marker for crRNA expression. The reporter plasmid contained a pSC101 replication origin, a kanamycin-selectable marker, and an yfp as the reporter gene regulated by a J23100 promoter.

The screening assay was used to quantify the functional effects of dCpf1 mutants systematically. In AsCpf1 with altered PAM specificity, mutated S542 and K607 residues interacted with the thymine nucleotides at the −2 and −3 PAM positions. Using the negative screening assay, we validated that the corresponding dFnCpf1 mutant (N607R/K671R) created by homologous alignment had a low activity on most expected high-GC PAM sites, and it exhibited lower PAM constrains than WT dFnCpf1. Therefore, a 750 bp DNA sequence (SEQ ID NO: 3) containing the PAM-interacting (PI) domains of dFnCpf1 mutants N607R, K671R, N607R/K671R through error-prone PCR to construct a dfncpf1 variants plasmid library. The mutagenesis library was introduced into host *E. coli* cells harboring a plasmid expressing crRNA and a plasmid carrying different SSSC PAMs upstream of the yfp gene. Expression of the dFnCpf1-crRNA system was induced using IPTG, and reduction in fluorescence was quantified to evaluate the PAM recognition and target binding efficiency of the dFnCpf1-crRNA complex (FIG. 1). The invention applies the negative screening assay to impose artificial selection pressure to screen mutants that could recognize different GC-rich PAM sequence.

Flow cytometry was used to screen mutants with significantly reduced fluorescence as follows: The *E. coli* strain DH5a strain was used in this study. *E. coli* strain was cultured in LB (10 g/L tryptone, 5 g/L yeast extract, 10 g/L NaCl) or M9 media (12.8 g/L Na2HPO4·7H2O, 3 g/L KH2PO4, 0.5 g/L NaCl, 1.67 g/L NH4Cl, 1 mM thiamine hydrochloride, 0.4% glucose, 0.2% casamino acids, 2 mM MgSO4, 0.1 mM CaCl2). LB was used as the growth media. Cells for flow cytometric fluorescence analysis were cultured in M9 media.

Bacterial cells were cultured overnight, diluted 196 times using the M9 medium containing three antibiotics, and later incubated for 3 h. After incubation, cells were diluted 1000 times in the M9 medium containing three antibiotics and 200 μM IPTG followed by shaking at 37° C. for 8 h. To stop protein expression prior to flow cytometry analysis, bacterial cells were diluted using PBS containing 2 mg/mL kanamycin. The fluorescence intensity of YFP was measured using a Calibur flow cytometer (BD Biosciences, CA, USA) with appropriate settings (FSC 440, SSC 260, FITC 480). Minimum 50,000 events were collected for each sample. The geometric mean of fluorescence intensity of each sample was analyzed using FlowJo software version 7.6.2 (Treestar, USA), and the autofluorescence of *E. coli* was subtracted for each sample. The resulting dFncpf1 mutant libraries were transformed into the *E. coli* DH5a cells harboring the reporter plasmid and the crRNA plasmid. The transformants were cultured overnight (~14 h), diluted, and induced by 200 μM IPTG for 6 h. Later, cells with relatively lower fluorescence (lower than an artificially defined threshold) were sorted into fresh LB medium using a BD Influx cell sorter (BD, USA). After 3 h of cell resuscitation, the sorted cells were plated on LB agar. The clones were picked and cultured further for flow cytometry (BD Fortessa, USA) based validation studies. Cells with relatively low fluorescence were sequenced and collected for the next mutant screening. A positive control (*E. coli* DH5a strain containing the pSC101-J23100-yfp plasmid) and negative control (*E. coli* DH5a strain containing the pSC101-J23100, pColE1-J23119-crRNA, and p15A-pTac-dfncpf1 plasmids) were used to set the appropriate gain for the fluorescence channel.

Directed evolution was employed to evolve the dFnCpf1 for binding to each of the eight possible SSSC (S=C,G) PAM target sequences in parallel. Finally, we obtained 86 mutants that effectively recognized the corresponding GC-rich PAM sequences respectively, compared to little or no activity for WT. In the invention, dFnCpf1 mutants with strong recognition ability of PAM CCCC and PAM CCGC is obtained, and the repression fold of YFP fluorescence value can reach more than 100 times (equivalent to the binding ability of wild-type dFnCpf1 for PAM TTTC). The dFnCpf1 mutants with strong recognition ability of PAM GCCG and PAM GCGC could inhibit the YFP fluorescence value by 60 or 70 times. The mutant with obvious recognition ability of PAM CGCC, GGCC, CGGC and GGGC could suppress the YFP fluorescence value by more than 30 times. The results are showed as Table 1:

TABLE 1

| All dFnCpf1 variants screened from the directed evolution | |
|---|---|
| | Repression fold |
| Mutants evolved from the PAM CCCC pathway | |
| E566V/K671R/D751G(refer to VRG) | 51.22 |
| VRG/E635K | 65.20 |
| VRG/N580H | 63.17 |
| VRG/N508H/F570L | 81.92 |
| VRG/N508H/F570L/E752V | 91.30 |
| VRG/N508H/F570L/N637S | 116.43 |
| VRG/N508H/F570L/N553D | 102.18 |
| VRG/N508H/F570L/I542V | 93.26 |
| VRG/N508H/F570L/I542V/E559G | 102.77 |
| Mutants evolved from the PAM GCCC pathway | |
| VRG | 20.34 |
| VRG/F570L | 37.60 |
| VRG/E635K | 37.53 |
| VRG/F570L/E756G | 36.08 |
| VRG/F570L/N634D | 40.90 |
| VRG/F570L/D687N | 57.09 |
| VRG/F570L/N634D/K611R | 61.30 |
| VRG/F570L/N634D/R755K | 61.84 |
| VRG/F570L/N634D/E767G | 54.26 |
| Mutants evolved from the PAM CCGC pathway | |
| VRG/S518G | 155.27 |
| VRG/S546R | 143.85 |
| VRG/L537I | 33.01 |
| VRG/S518G/K639R | 159.86 |

TABLE 1-continued

All dFnCpf1 variants screened from the directed evolution

| | Repression fold |
|---|---|
| VRG/S518G/K639R/K719R | 135.95 |
| VRG/L537I/K639R/F565L | 140.00 |
| VRG/L537I/F565L/K639R/K719R | 143.32 |
| VRG/L537I/F565L/N634D/K719R | 151.20 |
| Mutants evolved from the PAM GCGC pathway | |
| VRG/F570L | 68.77 |
| VRG/S546R | 62.69 |
| VRG/F570L/E686D | 77.17 |
| VRG/F570L/N634D/E686D | 68.68 |
| VRG/F570L/I575M/E686D | 63.22 |
| VRG/F570L/N634D/L572I | 63.23 |
| VRG/F570L/N634D/F596Y | 68.05 |
| Mutants evolved from the PAM CGCC pathway | |
| VRG/K613N (refer toVRGN) | 10.87 |
| VRGN/F570L | 27.31 |
| VRGN/F570L/N637S | 23.25 |
| VRGN/N534K/N637S | 20.39 |
| VRGN/N637S/N534K/G664V | 64.75 |
| VRGN/N637S/N534K/G664S | 38.40 |
| Mutants evolved from the PAM GGCC pathway | |
| VRGN/F570L/G664S | 35.06 |
| VRGN/F570L/G664S/N637Y | 62.14 |
| VRGN/F570L/G664S/F710S | 29.30 |
| VRGN/F570L/G664S/K647R/I728L | 40.78 |
| VRGN/F570L/G664S/A619V/S729R | 36.03 |
| Mutants evolved from the PAM CGGC pathway | |
| VRGN/Y724C | 32.83 |
| VRGN/Y724C/F570L | 47.10 |
| VRGN/Y724C/D522V/K650R | 33.19 |
| VRGN/Y724C/D616N | 33.22 |
| VRGN/Y724C/K505N/F570L | 42.95 |
| VRGN/Y724C/F570L/I582V | 42.26 |
| VRGN/Y724C/F570L/E715D | 38.75 |
| Mutants evolved from the PAM GGGC pathway | |
| VRGN/Y724C | 15.37 |
| VRGN/Y724C/Q509R | 32.09 |
| VRGN/Y724C/F570L | 36.37 |
| VRGN/Y724C/F570L/R690I/L662I | 45.41 |
| VRGN/Y724C/F570L/R690I/D625E | 41.59 |

Embodiment 2

1. PAM Preference Profiles Analysis

To determine PAM compatibilities in acquired mutants (separately evolved based on different GC-rich PAMs), eight M1 variants with the highest activity in the corresponding PAM trajectories were assessed for the global 64 PAM preferences (NNNC, the last base of PAM sequence is determined as C due to the weak preference) and later compared with WT dFnCpf1. A randomized PAM library (NNNC) was constructed through PCR and Gibson ligation. The 64 PAM plasmids were transformed separately into competent *E. coli* DH5α cells harboring dFnCpf1 mutants and crRNA plasmids. The fluorescence intensity of YFP was measured using a Calibur flow cytometer and the data was analyzed using FlowJo. The PAM preference profiles were analyzed and displayed using Matlab.

Figure 3:
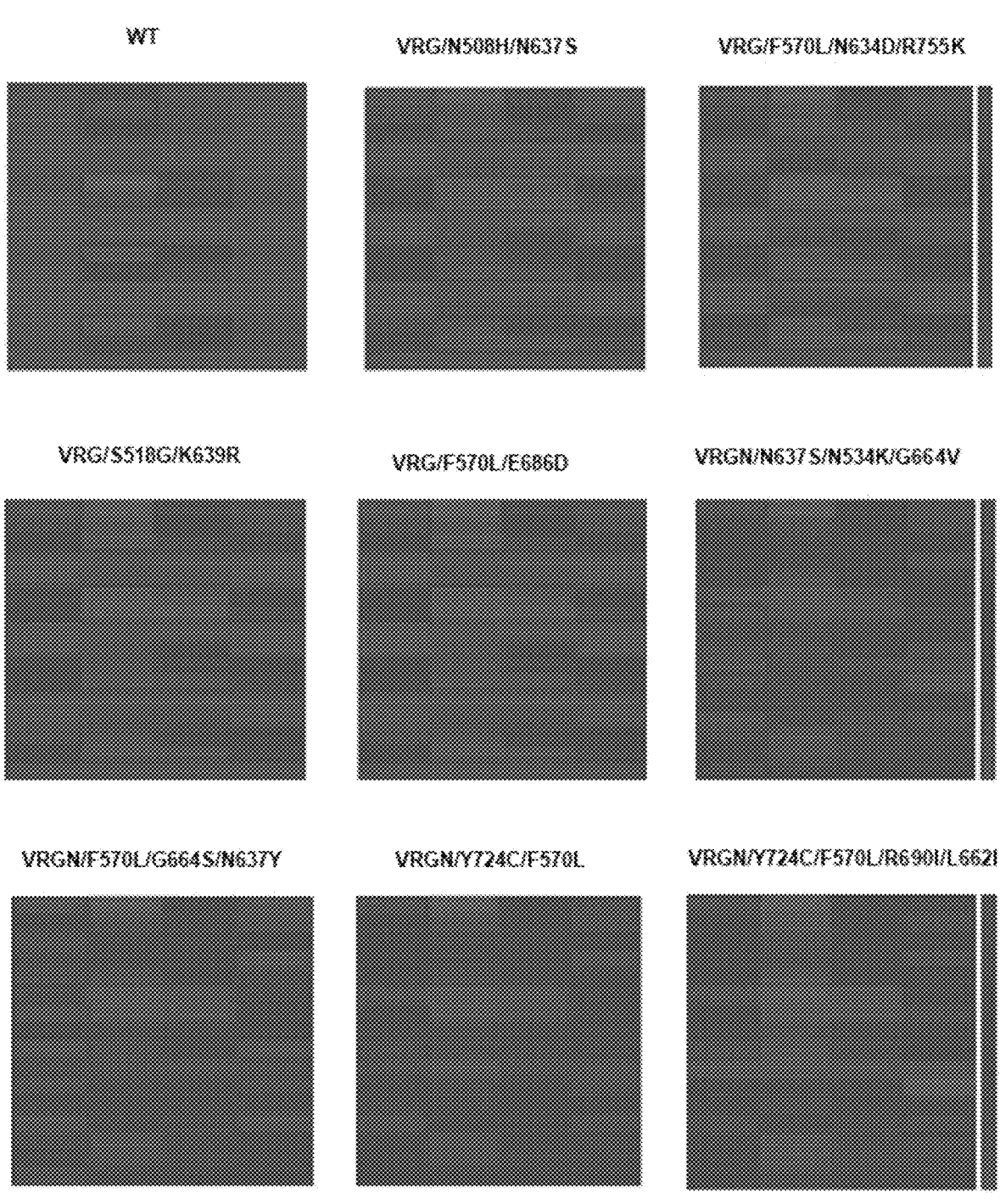
FIG. 3. PAM preference profiles for WT dFnCpf1 and eight selected mutants. The variants with the highest activity in the corresponding PAM trajectories were assessed for the global 64 PAM preferences (NNNV, V is not included due to the weak preference) and later compared with WT dFnCpf1. The mutants dFnCpf1 (VRG/N508H/N637S), dFnCpf1 (VRG/F570L/N634D/R755K), dFnCpf1 (VRG/S518G/K639R), dFnCpf1 (VRG/F570L/E686D) were selected from mutants obtained by directed evolution that recognize PAM GCCG, CCGC, GCGC and CGCC (SCSC), respectively. The mutants dFnCpf1 (VRGN/N637S/N534K/G664V), dFnCpf1 (VRGN/F570L/G664S/N637Y), dFnCpf1 (VRGN/Y724C/F570L), dFnCpf1 (VRGN/Y724C/F570L/R690I/L662I) were selected from mutants obtained by directed evolution that recognize PAM CGCC, GGCC, CGGC and GGGC (SGSC), respectively. VRG refers to the mutations E566V, K671R and D751G, besides N refers to the additional mutation K613N. YFP fluorescence intensity after 200 μM IPTG induction was used as the characterization value of PAM preference profiles.

As expected, WT dFnCpf1 was found to be the most effective for NTTC PAMs, especially for the TTTC PAM. WT dFnCpf1 also targeted other PAM sequences, including NCTC, AATC, and TTCC, but at lower rates (FIG. 3, Table 2). By contrast, the variants that can recognize SCSC PAMs showed the highest activity at NCCC and NCTC PAMs, compared to little or no activity for WT (FIG. 3). Surprisingly, the variants that can recognize SGSC PAMs were active at almost all 64 PAMs, especially the GC-rich PAMs, although the protein activity declined (FIG. 3, Table 2). We observed that the mutant dFnCpf1 (VRGN/Y724C/F570L/R690I/L662I), which was selected from the variants that could recognize GGGC PAM, had 52 effective identification tags (YFP fluorescence value <200) out of all 64 NNNC sites (81.3%) (Table 2). Furthermore, the mutant could effectively recognize 28 PAMs out of the 32 (87.5%) GC-rich PAMs (two or more C/G within −2 to −4 bits of PAM sequence) (Table 2). Thus, based on these outcomes, the dFnCpf1 (VRGN/Y724C/F570L/R690I/L662I) variant, obtained in this study with a significantly expanded targeting range (approximately 10 folds), was referred to as broad-spectrum dFnCpf1 (bsdFnCpf1). Besides, the other three mutants (VRGN/N637S/N534K/G664V, VRGN/F570L/G664S/N637Y, VRGN/Y724C/F570L) that could recognize SGSC PAMshad a 5-fold wider range of PAM than the wild-type.

Sequences of bsdFnCpf1 is provided as follows (SEQ ID NO:4):

```
ATGTCAATTTATCAAGAATTTGTTAATAAATATAGTTTAAGTAAAACTCTAAGATTTG

AGTTAATCCCACAGGGTAAAACACTTGAAAACATAAAAGCAAGAGGTTTGATTTT

AGATGATGAGAAAGAGCTAAAGACTACAAAAAGGCTAAACAAATAATTGATAAA

TATCATCAGTTTTTTATAGAGGAGATATTAAGTTCGGTTTGTATTAGCGAAGATTTAT

TACAAAACTATTCTGATGTTTATTTTAAACTTAAAAAGAGTGATGATGATAATCTAC

AAAAAGATTTTAAAAGTGCAAAAGATACGATAAAGAAACAAATATCTGAATATATA

AAGGACTCAGAGAAATTTAAGAATTTGTTTAATCAAAACCTTATCGATGCTAAAAA

AGGGCAAGAGTCAGATTTAATTCTATGGCTAAAGCAATCTAAGGATAATGGTATAG

AACTATTTAAAGCCAATAGTGATATCACAGATATAGATGAGGCGTTAGAAATAATCA

AATCTTTTAAAGGTTGGACAACTTATTTTAAGGGTTTTCATGAAAATAGAAAAAAT

GTTTATAGTAGCAATGATATTCCTACATCTATTATTTATAGGATAGTAGATGATAATTT

GCCTAAATTTCTAGAAAATAAAGCTAAGTATGAGAGTTTAAAAGACAAAGCTCCA

GAAGCTATAAACTATGAACAAATTAAAAAAGATTTGGCAGAAGAGCTAACCTTTG
```

-continued

```
ATATTGACTACAAAACATCTGAAGTTAATCAAAGAGTTTTTTCACTTGATGAAGTT

TTTGAGATAGCAAACTTTAATAATTATCTAAATCAAAGTGGTATTACTAAATTTAATA

CTATTATTGGTGGTAAATTTGTAAATGGTGAAAATACAAAGAGAAAAGGTATAAAT

GAATATATAAATCTATACTCACAGCAAATAAATGATAAAACACTCAAAAAATATAAA

ATGAGTGTTTTATTTAAGCAAATTTTAAGTGATACAGAATCTAAATCTTTTGTAATT

GATAAGTTAGAAGATGATAGTGATGTAGTTACAACGATGCAAAGTTTTTATGAGCA

AATAGCAGCTTTTAAAACAGTAGAAGAAAAATCTATTAAAGAAACACTATCTTTAT

TATTTGATGATTTAAAAGCTCAAAAACTTGATTTGAGTAAAATTTATTTTAAAAATG

ATAAATCTCTTACTGATCTATCACAACAAGTTTTTGATGATTATAGTGTTATTGGTAC

AGCGGTACTAGAATATATAACTCAACAAATAGCACCTAAAAATCTTGATAACCCTA

GTAAGAAAGAGCAAGAATTAATAGCCAAAAAAACTGAAAAGCAAAATACTTATC

TCTAGAAACTATAAAGCTTGCCTTAGAAGAATTTAATAAGCATAGAGATATAGATAA

ACAGTGTAGGTTTGAAGAAATACTTGCAAACTTTGCGGCTATTCCGATGATATTTG

ATGAAATAGCTCAAAACAAAGACAATTTGGCACAGATATCTATCAAATATCAAAAT

CAAGGTAAAAAAGACCTACTTCAAGCTAGTGCGGAAGATGATGTTAAAGCTATCA

AGGATCTTTTAGATCAAACTAATAATCTCTTACATAAACTAAAAATATTTCATATTAG

TCAGTCAGAAGATAAGGCAAATATTTTAGACAAGGATGAGCATTTTTATCTAGTATT

TGTGGAGTGCTACCTTGAGCTAGCGAATATAGTGCCTCTTTATAACAAAATTAGAA

ACTATATAACTCAAAAGCCATATAGTGATGAGAAATTTAAGCTCAATTTTGAGAACT

CGACTTTGGCTAATGGTTGGGATAAAAATAATGAGCCTGACAATACGGCAATTTTA

TTTATCAAAGATGATAAATATTATCTGGGTGTGATGAATAAGAAAAATAACAAAATA

TTTGATGATAAAGCTATCAAAGAAAATAAAGGCGAGGGTTATAAAAAAATTGTTTA

TAAACTTATACCTGGCGCAAATAAAATGTTACCTCGTGTTTTCTTTTCTGCTAAATC

TATAAAATTTTATAATCCTAGTGAAGATATACTTATAATAAGAAATCATTCCACACAT

ACAAAAAATGGTAGTCCTCAAAAAGGATATGAAAAATTTGAGTTTAATATTGAAGA

TTGCCGAAAATTTATAGATTTTTGTAAACAGTCTATAAGTAAGCATCCGGAGTGGA

AAGATTTTGGATTTAGATTTTCTGATACTCAAAGATATAATTCTATAGGTGAATTTTA

TAGAGAAGTTGAAAATCAAGGCTACAAACTAACTTTTGAAAATATATCAGAGAGC

TATATTGATAGCGTAGTTAATCAGGGTAAATTGTACCTATTCCAAATCTATAATAAAG

ATTTTTCAGCTTATAGCAAAGGGCGACCAAATCTACATACTTTATATTGGAAAGCGC

TGTTTGATGAGAGAAATCTTCAAGATGTGGTTTATAAGCTAAATGGTGAGGCAGAG

CTTTTTTATCGTAAACAATCAATACCTAAAAAAATCACTCACCCAGCTAAAGAGGC

AATAGCTAATAAAAACAAAGATAATCCTAAAAAAGAGAGTGTTTTTGAATATGATT

TAATCAAAGATAAACGCTTTACTGAAGATAAGTTTTTCTTTCACTGTCCTATTACAA

TCAATTTTAAATCTAGTGGAGCTAATAAGTTTAATGATGAAATCAATTTATTGCTAA

AAGAAAAAGCAAATGATGTTCATATATTAAGTATAGCAAGAGGTGAAAGACATTTA

GCTTACTATACTTTGGTAGATGGTAAAGGCAATATCATCAAACAAGATACTTTCAAC

ATCATTGGTAATGATAGAATGAAAACAAACTACCATGATAAGCTTGCTGCAATAGA

GAAAGATAGGGATTCAGCTAGGAAAGACTGGAAAAAGATAAATAACATCAAAGA

GATGAAAGAGGGCTATCTATCTCAGGTAGTTCATGAAATAGCTAAGCTAGTTATAG
```

-continued

```
AGTATAATGCTATTGTGGTTTTTGAGGATTTAAATTTTGGATTTAAAAGAGGGCGTT

TCAAGGTAGAGAAGCAGGTCTATCAAAAGTTAGAAAAAATGCTAATTGAGAAACT

AAACTATCTAGTTTTCAAAGATAATGAGTTTGATAAAACTGGGGGAGTGCTTAGAG

CTTATCAGCTAACAGCACCTTTTGAGACTTTTAAAAAGATGGGTAAACAAACAGG

TATTATCTACTATGTACCAGCTGGTTTTACTTCAAAAATTTGTCCTGTAACTGGTTTT

GTAAATCAGTTATATCCTAAGTATGAAAGTGTCAGCAAATCTCAAGAGTTCTTTAGT

AAGTTTGACAAGATTTGTTATAACCTTGATAAGGGCTATTTTGAGTTTAGTTTTGAT

TATAAAAACTTTGGTGACAAGGCTGCCAAAGGCAAGTGGACTATAGCTAGCTTTG

GGAGTAGATTGATTAACTTTAGAAATTCAGATAAAAATCATAATTGGGATACTCGA

GAAGTTTATCCAACTAAAGAGTTGGAGAAATTGCTAAAAGATTATTCTATCGAATAT

GGGCATGGCGAATGTATCAAAGCAGCTATTTGCGGTGAGAGCGACAAAAAGTTTT

TTGCTAAGCTAACTAGTGTCCTAAATACTATCTTACAAATGCGTAACTCAAAAACA

GGTACTGAGTTAGATTATCTAATTTCACCAGTAGCAGATGTAAATGGCAATTTCTTT

GATTCGCGACAGGCGCCAAAAAATATGCCTCAAGATGCTGATGCCAATGGTGCTTA

TCATATTGGGCTAAAAGGTCTGATGCTACTAGGTAGGATCAAAAATAATCAAGAGG

GCAAAAAACTCAATTTGGTTATCAAAAATGAAGAGTATTTTGAGTTCGTGCAGAAT

AGGAATAAC.
```

TABLE 2

PAM preference analysis profile data.YFP fluorescence intensity after
200 μM IPTG induction was used as the characterization value.

| PAM | WT | CCCC-M1 (VRG/N508H/N637S) | GCCC-M1 (VRG/F570L/ N634D/R755K) | CCGC-M1 (VRG/S518G/K639R) | GCGC-M1 (VRG/F570L/E686D) |
|---|---|---|---|---|---|
| AAAV | 3839.2 | 3921.2 | 3606.6 | 4136 | 3960.8 |
| ATAV | 2832.4 | 989.4 | 670.8 | 1287.2 | 1092.6 |
| ACAV | 2891.4 | 251.4 | 199.8 | 425.8 | 318.2 |
| AGAV | 4170.4 | 4149.2 | 3872.4 | 4457.8 | 4328.6 |
| TAAV | 3818.4 | 4167.4 | 3193.8 | 4063.2 | 3946.6 |
| TTAV | 1284.6 | 217.6 | 140.4 | 274 | 203.4 |
| TCAV | 3186.8 | 404.8 | 252.6 | 489.2 | 378.2 |
| TGAV | 3927 | 4490.4 | 4171.6 | 4264.4 | 4294.8 |
| CAAV | 4158 | 4275.6 | 3535.6 | 4252.4 | 4145.6 |
| CTAV | 1851.8 | 262.8 | 172.4 | 393 | 292 |
| CCAV | 3599 | 306.2 | 182.8 | 387.8 | 291.4 |
| CGAV | 4281.2 | 4429.4 | 3865.2 | 4561.4 | 4219.4 |
| GAAV | 4430.4 | 4945.2 | 4512 | 4609 | 4669.6 |
| GTAV | 2943.8 | 817 | 471.8 | 1433 | 1600.2 |
| GCAV | 2010.8 | 146 | 93.06 | 209.4 | 153.6 |
| GGAV | 4396 | 4816.8 | 4538.8 | 4545.4 | 4584.4 |
| AATV | 53.32 | 9.72 | 7.1 | 18 | 8.64 |
| ATTV | 31.78 | 33.92 | 30.02 | 41.46 | 34.42 |
| ACTV | 115.8 | 31.22 | 21.84 | 32.56 | 26.5 |
| AGTV | 2956.2 | 2154 | 1173.2 | 2302.4 | 2418 |
| TATV | 2113.2 | 965.4 | 516.8 | 1258 | 1004 |
| TTTV | 9.56 | 19.04 | 14.56 | 36.7 | 16.46 |
| TCTV | 39.56 | 22.94 | 16.22 | 18.74 | 16.82 |
| TGTV | 2064.4 | 1902.2 | 1507.4 | 2330.6 | 2227 |
| CATV | 3298.4 | 1272.4 | 694 | 1643.6 | 1534.8 |
| CTTV | 24.04 | 41.24 | 33.38 | 55.62 | 37.08 |
| CCTV | 130 | 32.96 | 29.92 | 42.06 | 32.62 |
| CGTV | 3404.2 | 2714.6 | 2040 | 3260 | 3029.6 |
| GATV | 2673.6 | 982.2 | 612.6 | 1516.4 | 1387.8 |
| GTTV | 16.3 | 33.16 | 23.68 | 42.02 | 36.44 |
| GCTV | 74.1 | 25.28 | 24.04 | 30.72 | 26.34 |
| GGTV | 2458.8 | 3046.6 | 2279.2 | 3140.4 | 3041.2 |
| AACV | 3759.6 | 755.4 | 350.6 | 988.8 | 758.2 |
| ATCV | 1551.6 | 322.2 | 155 | 379 | 258 |
| ACCV | 912.6 | 43.26 | 40.5 | 71.76 | 50.56 |
| AGCV | 3878.4 | 3129.4 | 2253.6 | 3450.8 | 3125.6 |

TABLE 2-continued

| | | PAM preference analysis profile data.YFP fluorescence intensity after 200 µM IPTG induction was used as the characterization value. | | |
|---|---|---|---|---|
| TACV | 3527.6 | 1287.6 | 733.4 | 1640.6 | 1607.4 |
| TTCV | 50.1 | 32.42 | 26.3 | 49.24 | 33.06 |
| TCCV | 186.4 | 16.62 | 14.8 | 21.5 | 16.94 |
| TGCV | 4192.6 | 4230.4 | 3545.6 | 3401.6 | 4312 |
| CACV | 3403.4 | 537.8 | 236.6 | 787.6 | 516.2 |
| CTCV | 303.6 | 76.36 | 57.4 | 113.4 | 85.08 |
| CCCV | 816 | 37.14 | 30.4 | 51.68 | 37.68 |
| CGCV | 4079.2 | 3433.8 | 2528.6 | 3728.6 | 3042.6 |
| GACV | 3428.6 | 876.4 | 447.6 | 1187.8 | 888.6 |
| GTCV | 224 | 108.72 | 66.48 | 137 | 116.2 |
| GCCV | 466.2 | 31.2 | 27.66 | 99.44 | 34 |
| GGCV | 3518 | 3423 | 2746.2 | 3416.6 | 3416.2 |
| AAGV | 3882.4 | 3735 | 2621.6 | 3779.8 | 3554.4 |
| ATGV | 3581.8 | 1727.8 | 1222.2 | 2032.2 | 1813.8 |
| ACGV | 2907.8 | 135 | 84.62 | 208.8 | 141.2 |
| AGGV | 3815 | 4128.8 | 3860.2 | 4174.6 | 3920 |
| TAGV | 4256.2 | 2930.6 | 2195 | 3358.6 | 3257.2 |
| TTGV | 2314.8 | 392.6 | 360 | 626.4 | 493.8 |
| TCGV | 1421.6 | 46.04 | 179.46 | 75.3 | 59.62 |
| TGGV | 3952.6 | 4305.8 | 4220.2 | 4268.4 | 4209.8 |
| CAGV | 3824.8 | 3586.8 | 2651.2 | 3710.2 | 3661 |
| CTGV | 2276 | 260 | 154 | 376 | 326 |
| CCGV | 2731.6 | 220.8 | 164.6 | 37.74 | 69.88 |
| CGGV | 4255 | 4384.4 | 3914.2 | 4349.4 | 4288.8 |
| GAGV | 4204.2 | 3954.8 | 3281.2 | 4179.4 | 4135.6 |
| GTGV | 1814.2 | 268 | 228 | 451.4 | 356.4 |
| GCGV | 1769.8 | 44.76 | 53.5 | 96.02 | 68.16 |
| GGGV | 3845.5 | 4366.6 | 4116.6 | 4299.4 | 4276.6 |

| PAM | CGCC-M1 (VRGN/N637S/ N534K/G664V) | GGCC-M1 (VRGN/F570L/ G664S/N637Y) | CGGC-M1 (VRGN/Y724C/F570L) | GGGC-M1 (VRGN/Y724C/F570L/ R690I/L662I) |
|---|---|---|---|---|
| AAAV | 2510.88 | 3513.4 | 2033 | 2045 |
| ATAV | 164.80 | 508.2 | 233.4 | 176.8 |
| ACAV | 327.60 | 1224 | 386.6 | 359 |
| AGAV | 212.20 | 594.2 | 302.4 | 196 |
| TAAV | 246.60 | 767 | 506 | 390.2 |
| TTAV | 32.10 | 57.5 | 33.12 | 30.26 |
| TCAV | 1343.20 | 2327.4 | 345.2 | 337 |
| TGAV | 136.80 | 361.6 | 139.8 | 123.4 |
| CAAV | 1113.33 | 2816.4 | 1160.6 | 1296.8 |
| CTAV | 34.76 | 57.5 | 35.46 | 27.32 |
| CCAV | 863.00 | 1611.6 | 200 | 159 |
| CGAV | 85.14 | 136.8 | 64.56 | 63.58 |
| GAAV | 3166.40 | 4037.4 | 2040.6 | 1605.2 |
| GTAV | 710.60 | 673.8 | 114 | 125.8 |
| GCAV | 118.20 | 260.2 | 103 | 93.48 |
| GGAV | 806.60 | 1350.6 | 296.2 | 239 |
| AATV | 9.70 | 11.62 | 10.1 | 5.62 |
| ATTV | 39.18 | 36.62 | 38.26 | 26.22 |
| ACTV | 67.82 | 81.28 | 61.6 | 49.16 |
| AGTV | 82.08 | 88.56 | 74.68 | 51.16 |
| TATV | 32.70 | 36.06 | 47.28 | 32.92 |
| TTTV | 19.26 | 16.14 | 17.26 | 14.38 |
| TCTV | 35.06 | 28.38 | 28 | 20.92 |
| TGTV | 66.53 | 71.04 | 72.66 | 46.4 |
| CATV | 47.68 | 48.96 | 60.8 | 34.94 |
| CTTV | 54.80 | 48.14 | 27.36 | 30.36 |
| CCTV | 82.72 | 125.2 | 65.92 | 66.42 |
| CGTV | 64.56 | 71.82 | 63.86 | 42.58 |
| GATV | 75.42 | 143.6 | 96.14 | 93.44 |
| GTTV | 33.46 | 29.86 | 36.6 | 23.94 |
| GCTV | 38.00 | 39.98 | 41.66 | 30.62 |
| GGTV | 71.16 | 81.08 | 84.8 | 53.56 |
| AACV | 88.08 | 154 | 135.4 | 75.42 |
| ATCV | 109.92 | 148.2 | 173 | 88.66 |
| ACCV | 150.60 | 144 | 164.8 | 102.4 |
| AGCV | 117.00 | 153.4 | 168.4 | 104.6 |
| TACV | 157.40 | 320 | 207.8 | 254.6 |
| TTCV | 36.28 | 31.2 | 34.14 | 26.32 |
| TCCV | 34.16 | 32.12 | 35.42 | 30.56 |
| TGCV | 116.14 | 127.4 | 119.4 | 113 |
| CACV | 150.80 | 237 | 65.12 | 58.54 |
| CTCV | 37.16 | 36.12 | 44.12 | 32.72 |
| CCCV | 128.00 | 170 | 133.2 | 141.2 |
| CGCV | 69.64 | 84.72 | 98.8 | 67.08 |

TABLE 2-continued

PAM preference analysis profile data.YFP fluorescence intensity after
200 μM IPTG induction was used as the characterization value.

| | | | |
|---|---|---|---|
| GACV | 46.74 | 59.4 | 82.2 | 53.28 |
| GTCV | 56.98 | 72.36 | 93.12 | 54.84 |
| GCCV | 57.66 | 58.96 | 70.4 | 46.44 |
| GGCV | 100.63 | 99.8 | 121.2 | 80.42 |
| AAGV | 2551.80 | 3412.8 | 993.4 | 673.6 |
| ATGV | 1331.00 | 2340.8 | 1357 | 1442.6 |
| ACGV | 177.60 | 341 | 210.6 | 152.2 |
| AGGV | 2070.00 | 3179.4 | 1979.2 | 1812 |
| TAGV | 220.40 | 615.8 | 281.8 | 183.2 |
| TTGV | 483.80 | 667.8 | 165.6 | 155 |
| TCGV | 68.92 | 109.6 | 73.04 | 44.4 |
| TGGV | 140.20 | 265.4 | 148.2 | 101.6 |
| CAGV | 1877.40 | 2750.6 | 577.4 | 512 |
| CTGV | 41.36 | 48 | 35.6 | 26.4 |
| CCGV | 17.85 | 979.2 | 45.12 | 6.38 |
| CGGV | 102.94 | 144.2 | 90.14 | 62.66 |
| GAGV | 1309.60 | 2915.4 | 1528 | 1560.2 |
| GTGV | 79.08 | 84.6 | 64.8 | 45.42 |
| GCGV | 81.66 | 127.2 | 75.46 | 54.4 |
| GGGV | 141.40 | 204.4 | 146.2 | 121.6 |

Embodiment 3

The dfncpf1 gene in the screening system was replaced with apobec1-dfncpf1-ugi gene (for expressing base editor dFnCpf1-BE) or apobec1-bsdfncpf1-ugi gene (for expressing base editor bsdFnCpf1-BE). The base editing efficiency was verified in *Escherichia coli*. The ugi and apobec1 genes were synthesized by Genscript Inc. After 48 hours of IPTG induction, bacteria were collected to extract plasmids, and primers were designed to build a library for next-generation sequencing.

Figure 4:
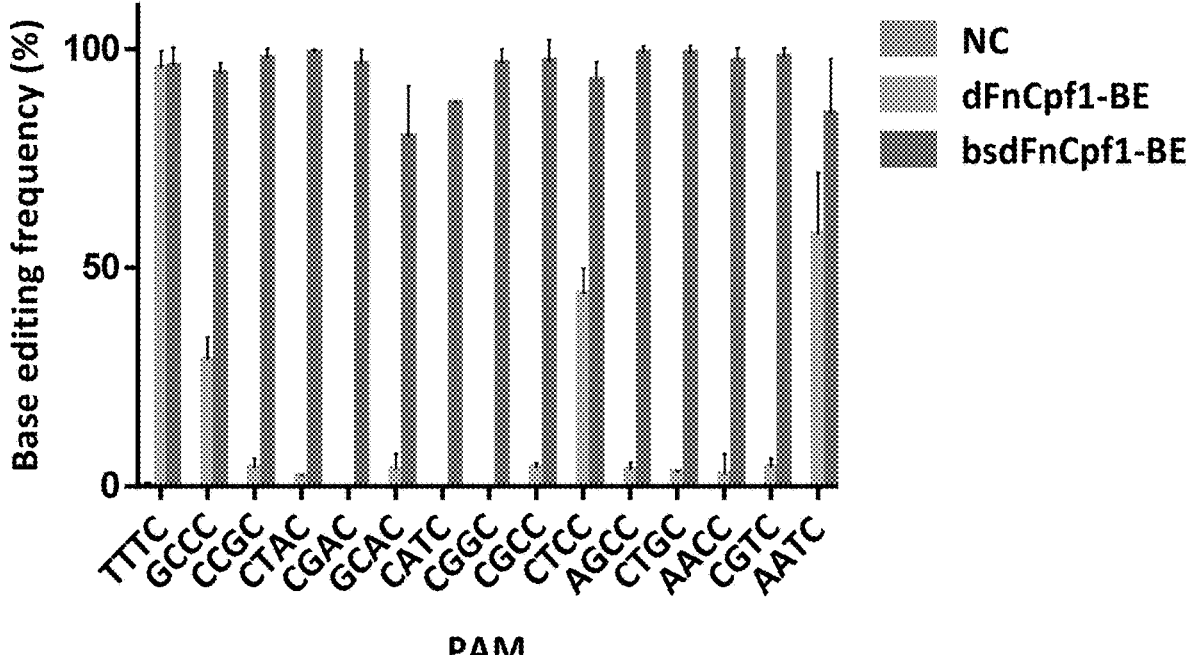
FIG. 4. Base editing mediated by bsdFnCpf1-BE and dFnCpf1-BE in *E. coli*. Determination of bsdFnCpf1-BE or dFnCpf1-BE induced base-editing frequency at the target site "GGGCACTCTCCAGATAGGGAT" (SEQ ID NO: 6) with different PAMs. Comparison of C to T editing efficiency of C8 at the target site between bsdFnCpf1-BE and dFnCpf1-BE, assessed by targeted deep sequencing.

The statistical results of next-generation sequencing are shown in FIG. 4. As expected, bsdFnCpf1-BE exhibited substantially improved C to T editing efficiency across all the 15 PAMs (FIG. 4). Compared with the wild-type base editor dFnCpf1-BE, bsdFnCpf1-BE has higher editing efficiency and wider PAM selectivity. These data validated the greatly improved PAM recognition range of bsdFnCpf1, which enabled bsdFnCpf1 to target more gene sequences.

The invention claimed is:

1. Mutants of CRISPR FnCpf1 or dFnCpf1 comprising the following mutations relative to wild-type FnCpf1 with the amino acid sequence shown in SEQ ID NO:2:

K671R/E566V/D751G/N508H/N637S,
K671R/E566V/D751G/F570L/N634D/R755K,
K671R/E566V/D751G/S518G/K639R,
K671R/E566V/D751G/F570L/E686D,
K671R/E566V/D751G/K613N/N637S/N534K/G664V,
K671R/E566V/D751G/K613N/F570L/G664S/N637Y,
K671R/E566V/D751G/K613N/Y724C/F570L,
K671R/E566V/D751G/K613N/Y724C/F570L/R690I/
L662I.

2. A nucleic acid encoding a mutant CRISPR FnCpf1 or dFnCpf1, wherein the mutant CRISPR FnCpf1 or dFnCpf1 is one of the following mutations relative to wild-type FnCpf1 with the amino acid sequence in SEQ ID NO: 2:

K671R/E566V/D751G/N508H/N637S,
K671R/E566V/D751G/F570L/N634D/R755K,
K671R/E566V/D751G/S518G/K639R,   K671R/E566V/
D751G/F570L/E686D,
K671R/E566V/D751G/K613N/N637S/N534K/G664V,
K671R/E566V/D751 G/K613N/F570L/G664S/N637Y,
K671R/E566V/D751G/K613N/Y724C/F570L,      and
K671R/E566V/D751G/K613N/Y724C/F570L/R690I/
L662I.

3. The nucleic acid of claim 2, wherein the nucleic acid has the sequence of SEQ ID NO: 4.

4. A vector comprising the nucleic acid of claim 2.

5. The vector of claim 4, wherein the vector is a vector for gene editing.

6. A recombinant cell line comprising the nucleic acid of claim 2.

* * * * *